United States Patent [19]

Hiraide et al.

[11] Patent Number: 5,292,774
[45] Date of Patent: Mar. 8, 1994

[54] SUBSTITUTION FLUID PREPARATION COMPRISING 3-HYDROXY-BUTYRIC ACID ($\beta$-HYDROXYBUTRIC ACID) AND ITS SALTS

[75] Inventors: Atsushi Hiraide, Osaka; Masami Katayama, Nishinomiya, both of Japan

[73] Assignee: Kanegafuchi Kagaku Kogyo Kabushiki Kaisha, Osaka, Japan

[21] Appl. No.: 53,314

[22] Filed: Apr. 27, 1993

Related U.S. Application Data

[63] Continuation of Ser. No. 751,619, Aug. 21, 1991, abandoned, which is a continuation of Ser. No. 272,955, Nov. 18, 1988, abandoned.

[30] Foreign Application Priority Data

Jul. 26, 1988 [JP] Japan .................. 63-185725

[51] Int. Cl.$^5$ .............................. A61K 31/19
[52] U.S. Cl. ................................ 514/557
[58] Field of Search ............ 424/678, 679, 680; 514/23, 561, 557

[56] References Cited

U.S. PATENT DOCUMENTS

| | | | |
|---|---|---|---|
| 4,579,955 | 4/1986 | Lammerant et al. | 514/554 |
| 4,663,166 | 5/1987 | Veech | 424/680 |
| 4,771,074 | 9/1988 | Lammerant et al. | 514/554 |
| 5,100,677 | 3/1992 | Veech | 514/557 |

OTHER PUBLICATIONS

The Journal of Nutrition, vol. 116, No. 1, Jan. 1986, pp. 149–156, The American Institute of Nutrition; A. Maiz et al. "Effect of DL-3-hydroxybutyrate infusions on leucine and glucose kinetics in burned rats receiving TPN".
Surgical Forum, vol. 39, 1988, editor M. Pannell, pp. 48–50, American College of Surgeons, Chicago, Ill., US; R. R. Jodoin et al.: "Determination of body composition from whole body electrical impedance".
The Journal of Clinical Investigation, vol. 55, No. 6, Jun. 1975, pp. 1382–1390, The American Society of Clinical Investigation, Inc.; R. S. Sherwin et al. "Effect of ketone infusions on amino acid and nitrogen metabolism in man".
Pawan, G. et al., "Effect of 3-Hydroxybutyrate in Obese Subjects on Very-Low-Energy and During Therapeutic Starvation", The Lancet Jan. (1983) pp. 15–17.
The Merck Index 10th edition cite #4727 p. 700 (1983).
Mainichi Newspaper, Nov. 18, 1987, Japanese Association for Acute Medicine, Atsushi Hiraide et al.
Journal of Japan Surgical Society, Feb. 25, 1988, Atsushi Hiraide et al.
15th Annual meeting of Japanese Association for Acute Medicine Mar. 22, 1988, Atsushi Hiraide et al.
Japanese Association of Parenteral and Enteral Nutrition proceeding, issued Dec. 1987, Atsushi Hiraide et al.
Journal of Japan Surgical Society, May 1, 1988, Atsushi Hiraide et al.
48th Annual Session of American Association for the Surgery of Trauma Abstract, Oct. 6–8, 1988, Atsushi Hiraide et al.

Primary Examiner—Frederick E. Waddell
Assistant Examiner—Raymond J. Henley, III
Attorney, Agent, or Firm—Armstrong, Westerman, Hattori, McLeland & Naughton

[57] ABSTRACT

The present invention provides a substitution fluid preparation which is characterized by containing at least one selected from 3-hydroxybutyric acid, 3-sodium hydroxybutyrate and 3-potassium hydroxybutyrate. The substitution fluid preparation of the present invention can be easily metabolized in the body of a patient to provide a good energy source and is also effective for suppressing increased protein catabolism in the living body.

4 Claims, 3 Drawing Sheets

SUBSTITUTION FLUID PREPARATION COMPRISING 3-HYDROXY-BUTYRIC ACID (β-HYDROXYBUTRIC ACID) AND ITS SALTS

This application is a continuation of application Ser. No. 07/751,619 filed Aug. 21, 1991, now abandoned which is a continuation of Ser. No. 07/272,955 filed Nov. 18, 1988, now abandoned.

BACKGROUND OF THE INVENTION

1. Field of the Invention

The present invention relates to a substitution fluid preparation, and more particularly to a substitution fluid composition which is applied as an energy source, for the suppression of increased protein catabolism in the living body and also for improvement of metabolic acidosis to traumatized patients or severely burned patients in the acute phase, post-operative patients, patients in hepatic insufficiency, patients unable to take foods orally, patients in the state of metabolic (except diabetes-induced) acidosis, all of whom have a common symptom of impaired carbohydrate metabolism.

2. Description of the Prior Art 3-hydroxybutyric acid as the principal ingredient of the substitution fluid composition of the present invention was first found in the urine of some diabetic patients in the form of (R)-3-hydroxybutyric acid and was then deemed to be a useless metabolite occurring in the living body under morbid conditions. Also, as fat-derived energy substrate the object of concern were long-chain fatty acids and the physiological significance of this substance had been rather neglected for a long time. Recently, however, the true physiological significance of this substance has come to be realized as a complementary substrate as substitute of glucose and also as a retainer of caloric homeostasis in the living body.

As to the significance of this substance as energy substrate, it is already known that it is a fat-derived energy substrate, that it is hydrophilic and has an extremely good migration-to-tissues behavior and that it has been used in preference to long-chain fatty acids or glucose in vitro experiments involving tissues of various kinds [(1) Forsey R. G. P., Reid. K. Brosnan J. T. Can. J., "Physiological Pharmacology," 65, 401–406, 1987; (2) Robinson A. M., Wiliamson D. H., "Physiological Reviews," 60 (1), 143–187, 1980], and judging from all these, it can be safely said that this substance is an excellent energy substrate.

When the supply of glucose is unavailable in the living body, it is already known that this substance provides a useful energy substrate, and there are also reports that (RS)-3-sodium hydroxybutyrate administered intravenously to patients under a "very-low-energy diets" therapy proved to be effective in suppressing protein catabolism [(1) Rawan G. L. S., Semple S. L. G., "Lancet," 1, 15–17, 1983; (2) Sherwin R. S., Hendler R. G., Felic P., "The Journal of Clinical Investigation," 55, 1382–1390). These are reports of the cases in which this substance was administered to the living body under the forced condition of scarcity of glucose. The present inventors, however, made rather extensive studies of traumatized patients or severely burned patients in the acute phase, post-operative patients with strong indications of surgical aggression, patients in hepatic insufficiency, patients unable to take foods orally, patients in the state of metabolic (except diabetes-induced) acidosis et al. and found and confirmed that many of such patients were falling into the state of abnormality of metabolism with regard to glucose, amino acid et cetera, this resulting in insufficient utilization of intravenously-administered nutrients such as sugar, amino acids and fat, and they were forced to use energy produced inside through decomposition of protein in their bodies and also that the levels in blood of alanine and glutamine resulting from decomposition of protein were increasing and due to the simultaneous loss of nitrogen, the cumulative nitrogen equilibrium in blood was markedly biased toward the minus side. Patients under such conditions are very likely to have their cells' immune function lowered and suffer from complication by serious infection diseases.

SUMMARY OF THE INVENTION

It is a primary object of the present invention to provide a substitution fluid preparation which patients can easily metabolize as an energy source and which is effective for suppressing increased protein catabolism in the living body.

Further objects and advantages of the present invention will become apparent to those skilled in the art from reading of the detailed description below.

After intensive studies the present inventors discovered that substitution fluid preparations containing at least one of 3-hydroxybutyric acid, 3-sodium hydroxybutyrate and 3-potassium hydroxybutyrate can accomplish the aforementioned objects and thus could complete this invention.

DETAILED DESCRIPTION OF THE INVENTION

Figure 1:
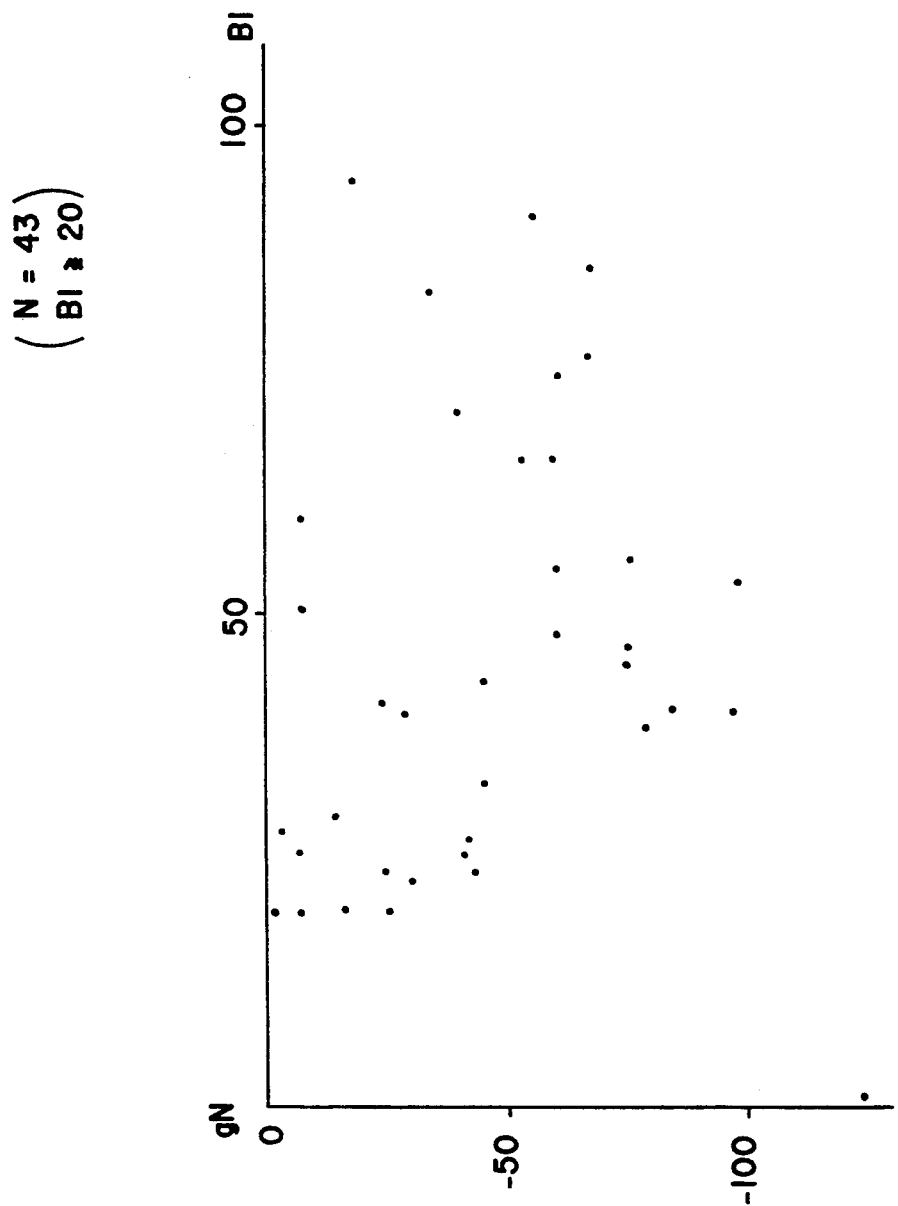
FIG. 1 shows the cumulative nitrogen equilibrium one week after injury in extensive cases of burn.

The present relates to provision of:

firstly, a substitution fluid preparation containing at least one of 3-hydroxybutyric acid, 3-sodium hydroxybutyrate and 3-potassium hydroxybutyrate;

secondly, a variation of the aforementioned substitution fluid preparation intended for addition to a substitution fluid for supplementing extracellular fluid or to a substitution fluid for maintaining good physical conditions, containing at least one of 3-hydroxybutyric acid, 3-sodium hydroxybutyrate and 3-potassium hydroxybutyrate dissolved in distilled water to be 0.5–2 mol/liter in concentration with pH controlled in a range of 6–8;

thirdly, a substitution fluid preparation prepared by adding inorganic electrolytes to the aforementioned first substitution fluid preparation and with its pH and osmotic pressure adjusted to be good for use as substitution fluid for supplementing extracellular fluid and made also good for direct intravenous administration;

fourthly, a substitution fluid preparation prepared by adding sugars and inorganic electrolytes to the aforementioned first substitution fluid preparation and with its calorific value, pH and osmotic pressure adjusted to be good for use as substitution fluid for maintaining good physical conditions and made also good for direct intravenous administration;

fifthly, a substitution fluid preparation prepared by adding amino acid or amino acid, sugars and inorganic electrolytes to the aforementioned first substitution fluid preparation and with its calorific value, pH and osmotic pressure adjusted to be good for use as substitution fluid for maintaining good physical conditions and made also good for direct intravenous administration; and sixthly, a substitution fluid preparation having combined in it any or all features of the aforementioned first through fifth substitution fluid preparations and made good for suppressing increased protein catabolism inside living body and for supplementing energy to traumatized patients or severely burned patients, post-operative patients, patients in hepatic insufficiency, patients having metabolic acidosis and patients unable to take foods orally.

As 3-hydroxybutyric acid used according to the present invention are included (RS)-3-hydroxybutyric acid and (R)-3-hydroxybutyric acid, while as 3-sodium hydroxybutyrate and 3-potassium hydroxybutyrate are included sodium salts and potassium salts of the aforementioned two kinds of acids, and these can be used either alone or in combination.

As inorganic electrolytes used as ingredient of substitution fluid for supplementing extracellular fluid and for maintaining good physical conditions are generally cited Ringer's substitution fluid preparation, alkali or alkali earth metal salts such as sodium chloride, potassium chloride and magnesium chloride which is added to various amino acid-fortified substitution fluid preparations; buffer salts such as sodium dihydrogen phosphate, potassium dihydrogen phosphate, sodium hydrogen phosphate and potassium hydrogen phosphate, and these, too, can be used either alone or in combination.

As sugars used in substitution fluid preparations are included, among others, reduced sugars such as grape sugar, maltose and fructose; non-reduced sugars such as D-sorbitol, mannitol and xylitol; polysaccharides such as dextran which is obtained by decomposition of starch, and these, too, can be used alone or in combination. As amino acids are included L-amino acid and its hydrochlorides, which, too, can be used either alone or in combination.

In preparing the substitution fluid of the present invention, each ingredient is first dissolved and the solution's pH and osmotic pressure ratio are adjusted. Especially when 3-hydroxybutyric acid is used, it itself has a high degree of acidity and pH adjustment by the use of sodium hydroxide is required.

For example, when addition to a substitution fluid for supplementing extracellular fluid or substitution fluid for maintaining good physical conditions is intended, 3-hydroxybutyric acid or its salt or both of the foregoings are to be dissolved in water preferably to a concentration of 0.5-2 mol/liter and its pH is to be preferably be adjusted to a range of 6-8. They are usable with both concentration and pH off the aforementioned ranges but as to concentration, handling is easy when it is within the aforementioned range, and as to pH, too, it is advisable to have it controlled within the given range, for in that case possible correction of the pH can be precluded.

Concrete examples of substitution fluid composition are given below.

(1) Substitution fluid composition intended for addition to substitution fluid for supplementing extracellular fluid or to substitution fluid for maintaining good physical conditions.
Composition (a)
3-hydroxybutyric acid [(RS) or (R)-form]: 5.2-10.4 wt. %
Sodium hydroxide: Quantity required to adjust pH of substitution fluid within a range of 6.0-8.0
Distilled water for injection: Quantity required for dilution to the aforementioned concentration
Osmotic pressure ratio: 3-6
Composition (b)
3-sodium hydroxybutyrate [(RS) or (R)-form]: 6.3-12.6 wt. %
Distilled water for injection: Quantity required for dilution to the aforementioned concentration
pH: 6.0-8.0
Osmotic pressure ratio: 3-6

(2) Substitution fluid preparation as supplementary liquid for extracellular fluid
Composition (a):
3-sodium hydroxybutyrate 0.35-1.0 wt. %
Sodium chloride 0.41-0.6 wt. %
Potassium chloride 0.03 wt. %
Calcium chloride 0.02 wt. %
To be dissolved with distilled water for injection.
pH: 4.5-8.0
Osmotic pressure ratio: 0.7-1.2
Composition (b):
3-hydroxybutyric acid 0.30-0.85 wt. %
Sodium hydroxide Quantity required to adjust the solution pH to the preset level.
Sodium chloride 0.41-0.6 wt. %
Potassium chloride 0.03 wt. %
Calcium chloride 0.02 wt. %
To be dissolved with distilled water for injection.
pH: 4.5-8.0
Osmotic pressure ratio: 0.7-1.2

(3) Substitution fluid preparation for maintaining good physical conditions (containing carbohydrates)
Composition (a):
3-sodium hydroxybutyrate [(RS) or (R)-form] 0.2-0.6 wt. %
Carbohydrates 2.0-5.0 wt. %
Sodium chloride 0.09 wt. %
Potassium chloride 0.149 wt. %
pH: 4.0-8.0
Osmotic pressure ratio: 1.0-1.6
Composition (b):
3-hydroxybutyrate [(RS) or (R)-form] 0.18-0.5 wt. %
Carbohydrates 2.0-5.0 wt. %
Sodium chloride 0.09 wt. %
Potassium chloride 0.149 wt. %
Sodium hydroxide The quantity required for adjustment to the preset pH
pH: 4.0-8.0
Osmotic pressure ratio: 1.0-1.6

The aforementioned compositions for the individual substitution fluid preparations are given only as examples and not to be taken as limiting.

The substitution fluid composition so prepared is filled in vials or like containers made of a plastic inert to the preparation and then, with the mouth or inlet sealed, sterilized with steam together with the container. Administration of the aforementioned substitution fluid preparation to patients is done in one of the ways exemplified below.

Case 1: 80-300 ml/day of the substitution fluid preparation (1) is first diluted by using not less than equivalent volume of distilled water for injection or an existing substitution fluid for supplementing extracellular fluid or for maintaining good physical conditions, and then administered at a rate not exceeding 100 milli equivalent/hour as 3-hydroxybutyric acid by intravenous drip injection.

Case 2: 500–1,000 ml of the preparation (2) per time is administered at a rate of 50–1,000 ml/hour by intravenous drip injection.

Case 3: 500–1,000 ml of the preparation (3) per time is administered as glucose at a rate of not more than 0.5 g/hour/kg (body weight) by intravenous drip injection.

Needless to say, however, the dose and administration rate for any such substitution fluid preparation are to be adjusted properly with the condition of the patient taken into due consideration.

Hereinafter, the present invention is described in greater detail, giving examples, but, needless to say, this invention is in no way limited thereby.

EXAMPLE 1

1 mol of (RS)-3-hydroxybutyric acid was dissolved in 100 ml of distilled water for injection and then neutralized with sodium hydroxide solution added dropwise to pH>8.0 and distilled water was further added to make up the whole to 1 liter. This was filled in a 1-liter plastic container and, with the mouth of the container sealed, sterilized by heat treatment for 2 hours at 110° C. The resulting liquid composition was 8.0 in pH and 6 in osmotic pressure ratio. Then distilled water for injection was added to the aforementioned 250 ml of liquid composition to make up the whole to 1 liter, again filled in the plastic container and sterilized in a like manner to prepare the substitution fluid preparation.

EXAMPLE 2

A substitution fluid preparation containing (RS)-3-sodium hydroxybutyrate and inorganic hydrolytes which is suited in composition for use as a substitution fluid for supplementing extracellular fluid was prepared in the following way.

(RS)-3-sodium hydroxybutyrate: 9.70 g
Sodium chloride: 4.1 g
Potassium chloride: 3.0 g
Calcium chloride: 2.0 g The above ingredients were dissolved with distilled water for injection to make up the whole to 1 liter. The resulting liquid composition was 7.2 in pH and 1 in osmotic pressure ratio. The electrolyte composition was as follows.

| | |
|---|---|
| $Na^+$ | 154 milli equivalent/liter |
| $K^+$ | 4 milli equivalent/liter |
| $Ca^{++}$ | 3 milli equivalent/liter |
| $Cl^-$ | 77 milli equivalent/liter |
| $CH_2CHCH_2COO^-$<br>$\|$<br>$OH$ | 77 milli equivalent/liter |

The above liquid composition was filled in a 1-liter plastic container and then, the mouth of the container was sealed, sterilized in the same way as described in Example 1.

EXAMPLE 3

A substitution fluid for maintaining good physical conditions containing (RS)-3-sodium hydroxybutyrate, grape sugar and inorganic electrolytes was prepared as follows.

Grape sugar: 43 g
(RS)-3-sodium hydroxybutyrate: 4.41 g
Sodium chloride: 0.9 g
Potassium chloride: 1.49 g
Sodium hydroxide Quantity needed to adjust pH to 7.0.

The above ingredients were dissolved and diluted with distilled water for injection to make up the whole to 1 liter. The resulting liquid composition was 7.0 in pH and 1.3 in osmotic pressure ratio. The electrolyte composition was as follows.

| | |
|---|---|
| $Na^+$ | 50 milli equivalent/liter |
| $K^+$ | 20 milli equivalent/liter |
| $Cl^-$ | 35 milli equivalent/liter |
| $CH_2CHCH_2COO^-$<br>$\|$<br>$OH$ | 35 milli equivalent/liter |

EXAMPLE 4

A substitution fluid preparation containing (R)-3-hydroxybutyric acid and inorganic electrolytes, whose composition is similar to that of a substitution fluid for supplementing extracellular fluid was prepared in the following way.

(R)-3-hydroxybutyric acid: 3.5 g
Sodium chloride: 6.0 g
Potassium chloride: 3.0 g
Calcium chloride: 2.0 g
Sodium hydroxide Quantity needed to adjust pH to 7.0.

The above ingredients were dissolved and diluted with distilled water for injection to make up the whole to 1 liter. The resulting liquid composition was 1 in osmotic pressure ratio. The electrolyte composition was as follows.

| | |
|---|---|
| $Na^+$ | 130 milli equivalent/liter |
| $K^+$ | 4 milli equivalent/liter |
| $Ca^{++}$ | 3 milli equivalent/liter |
| $Cl^-$ | 109 milli equivalent/liter |
| $CH_2CHCH_2COO^-$<br>$\|$<br>$OH$ | 28 milli equivalent/liter |

The above liquid composition was filled in a plastic container and, with the mouth of the container sealed, sterilized in the same way as described in Example 1.

EXAMPLE 5

A high-calorie maintaining type of substitution fluid preparation containing (R)-3-potassium hydroxybutyrate and (R)-3-sodium hydroxybutyrate was prepared in the following way. The composition of the substitution fluid preparation for maintenance (700 ml) was as follows.

Grape sugar: 175 g
(R)-3-potassium hydroxybutyrate: 3.1 g
(R)-3-sodium hydroxybutyrate: 1.8 g
Magnesium sulfate (heptahydrate): 1.24 g
Potassium dihydrogen phosphate: 0.66 g
Zinc sulfate (heptahydrate): 0.003 g
Potassium gluconate: 1.19 g The electrolyte composition of the above substitution fluid preparation was as follows.

| | |
|---|---|
| Na+ | 20 milli equivalent/liter |
| K+ | 30 milli equivalent/liter |
| Mg+ | 10 milli equivalent/liter |
| CH$_2$CHCH$_2$COO$^-$<br>   \|<br>   OH | 41.5 milli equivalent/liter |

APPLICATION EXAMPLE 1

The substitution fluid preparation of Example 1 was administered to a male severely burned patient in the acute phase (the burn had its center on the front side of the chest and of the total injured area of 33%, 13% was in the phase III) into the central vein for 3 hours at a rate of 25 microequivalent/liter. The result is shown in FIGS. 1 through 3.

FIG. 1 shows the progress of the cumulative nitrogen equilibrium in one week after the injury for patients not less than 20 in burn index, and from FIG. 1 it is apparent that the loss of nitrogen in the early phase of injury due to increased protein catabolism is unignorably large. It is known that alanine as a glycogenic amino acid flows out through the peripheral tissues, which was caused by protein catabolism.

Figure 2:
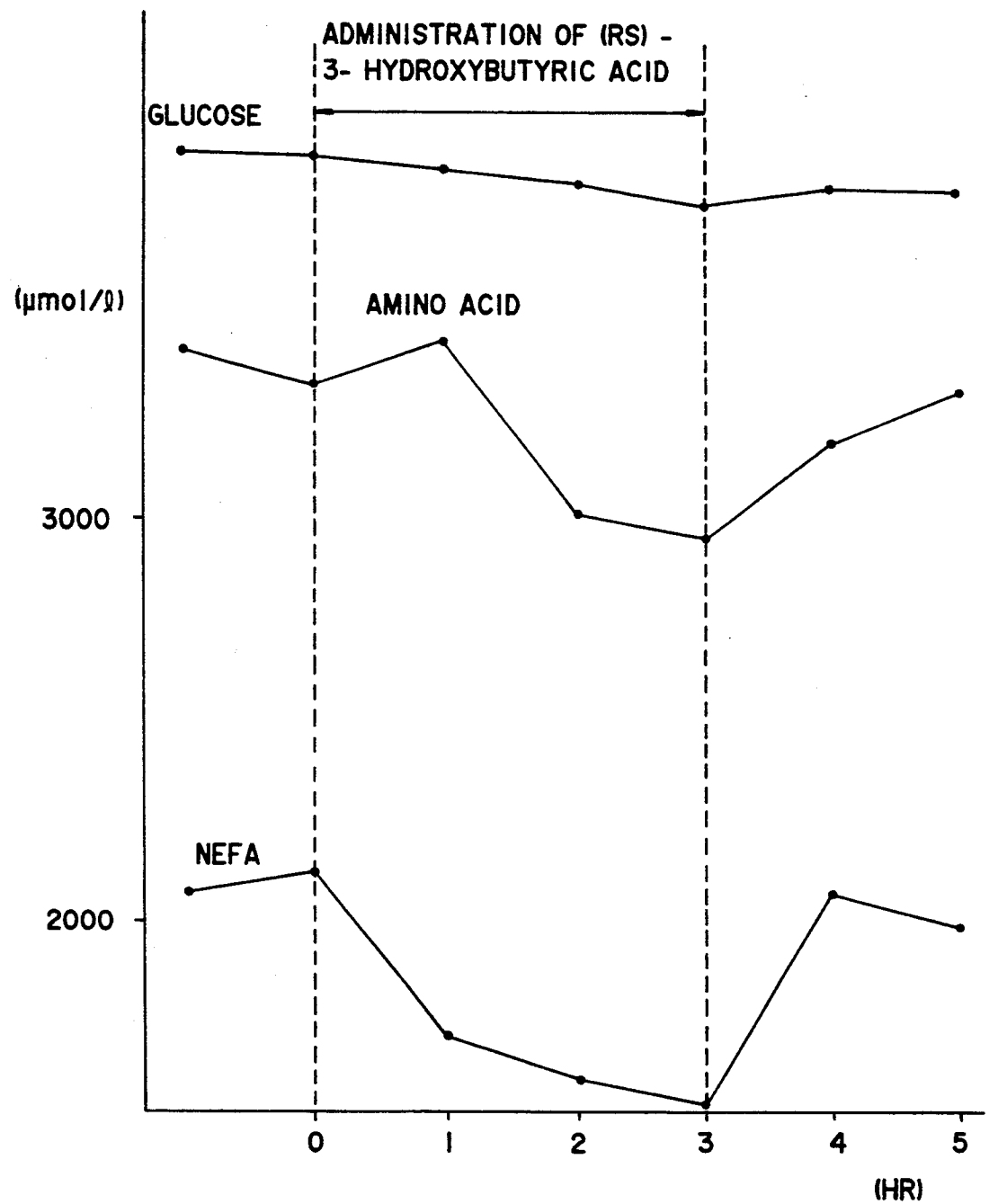
FIG. 2 is a graph showing the change-with-time of the concentrations in venous blood of glucose, amino acid and NEFA.

FIG. 2 shows that the concentrations in blood of the total amino acid and free fatty acid lower significantly as administration of (RS)-3-hydroxybutyric acid is continued.

Figure 3:
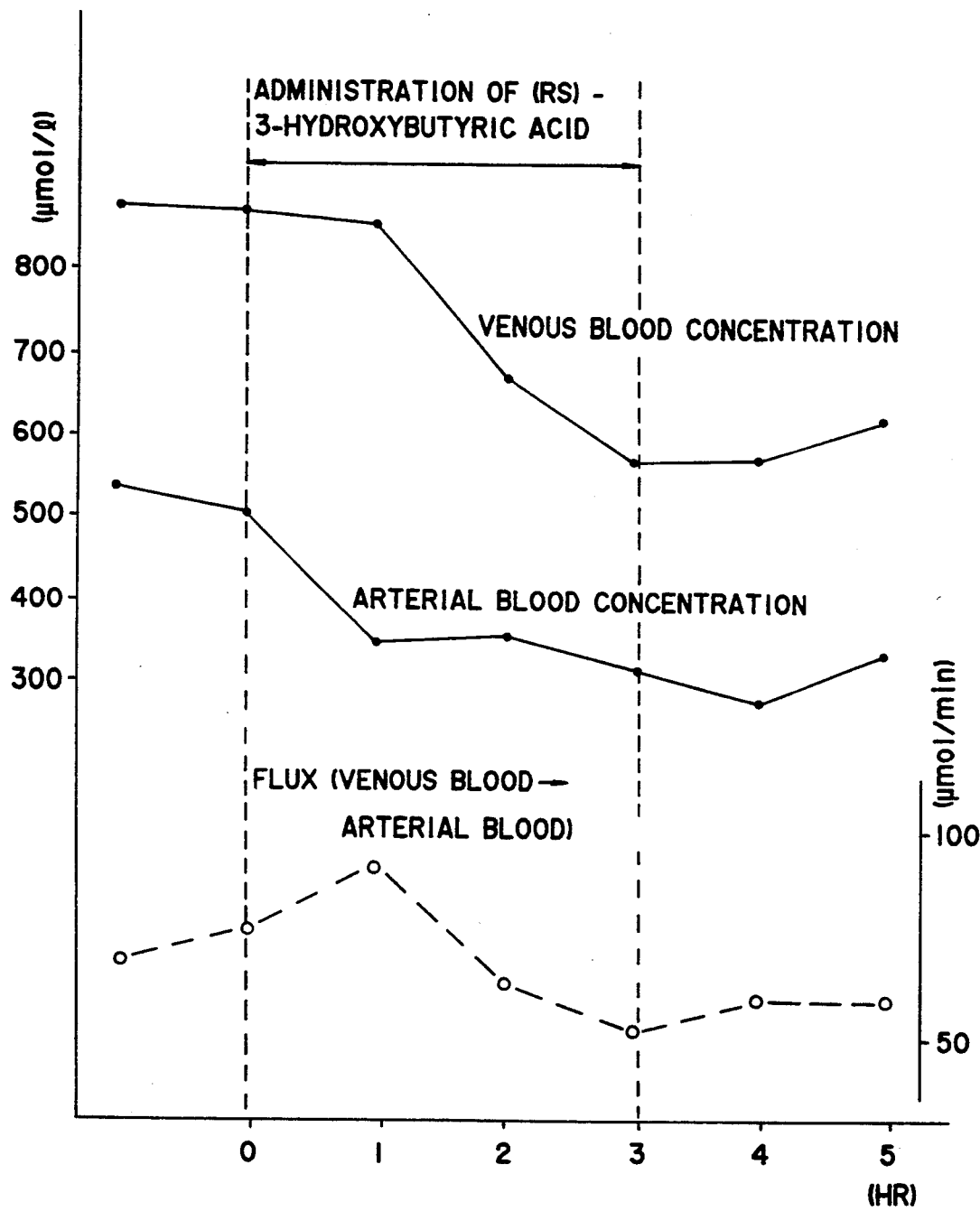
FIG. 3 is another graph showing the change-with-time of the concentration in blood of alanine.

FIG. 3 shows the concentration in blood of alanine and flux before and after administration of (RS)-3-hydroxybutyric acid, and from FIG. 3 it is apparent that the alanine concentration is markedly dropped as its administration is continued. The fact that of the amino acids present in blood, alanine closely related with protein catabolism has its concentration decreased significantly suggests that (RS)-3-hydroxybutyric acid administered when the butn is in the acute phase in which the patient is difficult to take nutrients is effective for saving of the own protein.

APPLICATION EXAMPLE 2

Study was made to see what kind of changes with regard to metabolism is caused by addition of (RS)-3-sodium hydroxybutyrate to a substitution preparation including glucose for maintaining good physical conditions.

In a test with 700 ml of Hicalic #2 ® (Termo) and 200 ml of Proteamin 12 ® (Tanabe Seiyaku) as the basic substitution fluid preparation, the solution described in Example 1 above prepared by dissolving (RS)-3-sodium hydroxybutyrate in distilled water for injection was added thereto, and then the mixed preparation was administered for 3 hours at a rate equivalent of 25 micromol/kg/min. of (RS)-3-sodium hydroxybutyrate and the change-with-time of the concentration of 3-hydroxybutyric acid, difference thereof between femoral artery and vein, blood sugar and alanine concentration were measured. The results are shown in Table 1.

TABLE 1

| | (Unit: micromol/liter) Change-with-time of concentration in blood | | | | |
|---|---|---|---|---|---|
| | 0 | 2 hrs | 3 hrs | 4 hrs | 5 hrs |
| Concentration of 3-hydroxybutyric acid | 213 ± 73 | 1382 ± 302 | 1432 ± 412 | 438 ± 121 | 313 ± 97 |
| Difference between femoral artery and vein | 44 ± 50 | 492 ± 263 | 432 ± 203 | 213 ± 112 | 23 ± 61 |
| Blood sugar concentration | 7683 ± 1232 | 7243 ± 1251 | 7462 ± 1513 | 7513 ± 1216 | 7522 ± 1317 |
| Alanine concentration | 332 ± 101 | 291 ± 111 | 273 ± 163 | 283 ± 121 | 300 ± 119 |
| Administration of 3-sodium hydroxybutyrate | ← (25 micromol/kg/min.) → | | | | |

From the test results shown in Table 1, it was recognized that the concentration in blood of (RS)-3-sodium hydroxybutyrate is increased even when it is added simultaneously with glucose, that the difference between femoral artery and vein is increased, this indicating that the administered (RS)-3-sodium hydroxybutyrate is consumed in the peripheral tissues of the lower limbs and that the concentration in blood of alanine is significantly lowered by administration of (RS)-3-sodium hydroxybutyrate. This, again, proves its effect to save the own protein.

APPLICATION EXAMPLE 3

A test was made to see if (R)-3-sodium hydroxybutyrate is more effective than (RS)-3-sodium hydroxybutyrate.

The test was carried out using hemorrhagic shock rats to compare the effects of administration of substitution fluid preparations for supplementing extracellular fluid containing (R)-3-sodium hydroxybutyrate and (RS)-3-sodium hydroxybutyrate respectively with those of Ringer's solution containing lactic acid as control.

(1) Preparation of hemorrhagic shock rat model

With the carotid artery cannulated, the blood pressure was kept at 40 mmHg by the reserved bottle method. The blood-removing time was set at 10 min. The shock continuing time was set at 30 min. and 1 ml of blood was taken every 10 min. (2) Preparation of substitution fluid preparations for supplementing extracellular fluid containing (R)-3-sodium hydroxybutyrate and (RS)-3-sodium hydroxybutyrate As electrolytes 0.41 wt. % of sodium chloride, 0.03 wt. % of potassium chloride and 0.02 wt. % of calcium chloride were used and the substitution fluid compositions were prepared with the contents of (R) and (RS)-3-sodium hydroxybutyrate adjusted to 0.96 wt. % respectively.

As control, a substitution fluid preparation containing sodium lactate of the following composition was prepared:

Sodium chloride 0.41 wt. %, potassium chloride 0.03 wt. %, calcium chloride 0.02 wt. % and sodium lactate 0.863 wt. %

Administration of these substitution fluid preparations for supplementing extracellular fluid into rats was started immediately after the start of blood-removal, and it was continued for 30 min. at a rate of 15 micromol/kg/min.

The concentrations of total 3-hydroxybutyric acid (containing a small amount of acetoxybutyric acid) in the blood samples taken up till 30 min. are shown in Table 2, and those of alanine in Table 3.

TABLE 2

| | (Unit: micromol/liter) | | | |
|---|---|---|---|---|
| | 0 | 10 min. | 20 min. | 30 min. |
| (R)-3-sodium-hydroxy-butyrate group | 483 ± 218 | 1846 ± 257 | 1762 ± 379 | 1850 ± 309 |
| (RS)-3-sodium-hydroxy-butyrate group | 435 ± 118 | 989 ± 380 | 931 ± 181 | 916 ± 201 |
| Sodium lactate group | 432 ± 117 | 293 ± 74 | 237 ± 49 | 228 ± 44 |

TABLE 3

| | (Unit: micromol/liter) | | | |
|---|---|---|---|---|
| | 0 | 10 min. | 20 min. | 30 min. |
| (R)-3-sodium-hydroxy-butyrate group | 458 ± 100 | 478 ± 107 | 491 ± 75 | 491 ± 80 |
| (RS)-3-sodium-hydroxy-butyrate group | 498 ± 126 | 559 ± 70 | 612 ± 80 | 710 ± 117 |
| Sodium lactate butyrate group | 438 ± 154 | 552 ± 146 | 666 ± 136 | 782 ± 195 |

The data in Table 2 and Table 3 above show the following facts.

i) Compared with the sodium lactate group, the (R) and (RS) groups have the concentration in blood of 3-hydroxybutyric acid increased, this value being significantly higher with the (R) group than with the (RS) group.

ii) Compared with the sodium lactate group, the (R) and (RS) groups are found having the rise of concentration better controlled as the shock progresses, this controlling effect being more significant with the (R) group than with the (RS) group.

iii) The (R) group has the alanine concentration-in-blood significantly better controlled than the (RS) group, having thus the own protein better saved as the shock progresses.

As described above, (R)-3-hydroxybutyric acid or (R)-3-sodium hydroxybutyrate (or potassium hydroxybutyrate) shows a marked effect for suppressing increased protein catabolism. Administration of the substitution fluid preparation of the present invention to patients such as those mentioned above, therefore, is highly effective in helping maintain their physical stamina and improve their immune function.

The substitution fluid preparation of the present invention is of quite a new type not having been studied heretofore in the field, being quite valuable from a physiological as well as nutrient viewpoint.

What is claimed is:

1. A method of supplying an energy source to a patient in a state of being substantially unable to metabolize carbohydrates, the method consisting of administering a substitution fluid preparation until said patient recovers the ability to metabolize carbohydrates, the preparation consisting essentially of:

an effective amount of at least one compound selected from the group consisting of (R)-3-hydroxybutyric acid, (RS)-3-hydroxybutyric acid, sodium (R)-3-hydroxybutyrate, sodium (RS)-3-hydroxybutyrate, potassium (R)-3-hydroxybutyrate and potassium (RS) 3-hydroxybutyrate, and a pharmaceutically acceptable carrier.

2. The method of claim 1, wherein said patient in a state of being substantially unable to metabolize carbohydrates is a traumatized patient, a severely burned patient, a post-operative patient, a patient in hepatic insufficiency, a patient having metabolic acidosis, or a patient unable to take foods orally.

3. A method for supplying an energy source to a patient in a state of being substantially unable to metabolize carbohydrates, which consists of administering a substitution fluid preparation consisting of
   (a) an effective amount of at least one compound selected from the group consisting of (R)-3-hydroxybutyric acid, (RS)-3-hydroxybutyric acid, sodium (R)-3-hydroxybutyrate, sodium (RS)-3-hydroxybutyrate, potassium (R)-3-hydroxybutyrate and potassium (RS)-3-hydroxybutyrate, and
   b) a pharmaceutically acceptable carrier, until said patient recovers the ability of metabolizing carbohydrates, and, after recovering said ability, administering a substitution fluid preparation consisting of
   (a) an effective amount of at least one compound selected from the group consisting of (R)-3-hydroxybutyric acid, (RS)-3-hydroxybutyric acid, sodium (R)-3-hydroxybutyrate, sodium (RS)-3-hydroxybutyrate, potassium (R)-3-hydroxybutyrate and potassium (RS)-3-hydroxybutyrate, and
   (b) an effective amount of at least one compound selected from the group consisting of amino acids, carbohydrates and inorganic salts,
   (c) a pharmaceutically acceptable carrier.

4. The method of claim 3, wherein said patient in a state of being substantially unable to metabolize carbohydrates is a traumatized patient, a severely burned patient, a post-operative patient, a patient in hepatic insufficiency, a patient having metabolic acidosis or a patient unable to take food orally.

* * * * *